(12) United States Patent
McCurdy

(10) Patent No.: US 12,391,773 B2
(45) Date of Patent: Aug. 19, 2025

(54) CARBON-NEGATIVE BIOPLASTIC

(71) Applicant: Charlotte McCurdy Research LLC, San Francisco, CA (US)

(72) Inventor: Charlotte Trumbull McCurdy, Locust Valley, NY (US)

(73) Assignee: CHARLOTTE MCCURDY RESEARCH LLC, San Francisco, CA (US)

(*) Notice: Subject to any disclaimer, the term of this patent is extended or adjusted under 35 U.S.C. 154(b) by 701 days.

(21) Appl. No.: 17/646,601

(22) Filed: Dec. 30, 2021

(65) Prior Publication Data
US 2022/0204653 A1 Jun. 30, 2022

Related U.S. Application Data

(60) Provisional application No. 63/132,275, filed on Dec. 30, 2020.

(51) Int. Cl.
*C08B 37/00* (2006.01)
*A01G 33/00* (2006.01)
(Continued)

(52) U.S. Cl.
CPC .......... *C08B 37/0003* (2013.01); *A01G 33/00* (2013.01); *C08B 37/0039* (2013.01);
(Continued)

(58) Field of Classification Search
CPC ............ C08B 37/0003; C08B 37/0039; C08B 37/0042; C08B 37/0084; A01G 33/00;
(Continued)

(56) References Cited

U.S. PATENT DOCUMENTS

| 2013/0186303 | A1 | 7/2013 | Budina |
| 2015/0196002 | A1* | 7/2015 | Friesth .................. A01G 7/045 315/297 |
| 2019/0048303 | A1* | 2/2019 | Maggiore ............ B67D 3/0012 |

FOREIGN PATENT DOCUMENTS

WO WO-2005101971 A2 * 11/2005 ............. G01N 21/45

OTHER PUBLICATIONS

BioGeometry® Nature's Own Design Language, "World's First Regional EMF Solution," 5 pages, retrieved from the Internet at: https://www.biogeometry.ca/home, Retrieved from the Internet on: Jan. 7, 2022.

(Continued)

*Primary Examiner* — Michael A Marcheschi
*Assistant Examiner* — Ashley Lopezlira
(74) *Attorney, Agent, or Firm* — Hamilton, Brook, Smith & Reynolds, P.C.

(57) ABSTRACT

Through sourcing net-primary productivity additive algae-based biomass feedstock, the exclusive use of renewable energy in processing, and the appropriate formulation and processing, a novel algae-derived bio-based plastic is both carbon-negative and provides some performance advantages over existing algae-based film plastics especially with regard to optical clarity. A system may be provided that produces a carbon-negative bioplastic. The production of the bioplastic in a process chamber may be controlled by an electronic controller. The electronic controller may be controlled by a host system, such a server. The electronic controller may be configured to direct production of the bioplastic in the process chamber using hydrocolloid, which is derived from algae.

19 Claims, 9 Drawing Sheets
(1 of 9 Drawing Sheet(s) Filed in Color)

(51) Int. Cl.
   *C12M 1/00*    (2006.01)
   *C12M 1/02*    (2006.01)
   *C12M 1/06*    (2006.01)
   *C12M 1/34*    (2006.01)

(52) U.S. Cl.
   CPC ...... *C08B 37/0042* (2013.01); *C08B 37/0084* (2013.01); *C12M 21/02* (2013.01); *C12M 23/22* (2013.01); *C12M 27/02* (2013.01); *C12M 29/04* (2013.01); *C12M 41/24* (2013.01); *C12M 41/40* (2013.01)

(58) Field of Classification Search
   CPC ...... C12M 21/02; C12M 23/22; C12M 27/02; C12M 29/04; C12M 41/24; C12M 41/40
   See application file for complete search history.

(56) References Cited

OTHER PUBLICATIONS

Wikipedia, Direct air capture, 6 pages, retrieved from the Internet at: https://en.wikipedia.org/wiki/Direct_air_capture, retrieved from the Internet on: Jan. 8, 2022.

Climeworks, "Join the journey to a climate-positive world," 3 pages, retrieved from the Internet at: https://climeworks.com/, Retrieved from the Internet on: Jan. 8, 2022.

\* cited by examiner

Prior Art

CARBON-NEGATIVE BIOPLASTIC

RELATED APPLICATION(S)

This application claims the benefit of U.S. Provisional Application No. 63/132,275, filed on Dec. 30, 2020. The entire teachings of the above application is incorporated herein by reference.

BACKGROUND

Globally, most plastics, both by volume and value, are synthesized from fossil fuel feedstocks (e.g., petroleum, natural gas, coal). As such, the production of these plastics causes the release of carbon into the biosphere and atmosphere, which in turn contributes to greenhouse gas emissions and the destructive effects of climate change. These emissions occur at the mining site of raw materials, at the manufacturing site of the refined material, and at the end of life of the plastic whether it is incinerated, landfilled or leeks into natural environments. The production of most conventional bio-based plastics contributes to greenhouse gas emissions because either the feedstock comes from a fossil-fuel intensive agricultural model (e.g., corn or soy-based bio-based plastics) or requires carbon-emitting deforestation to increase production (e.g., palm oil or virgin forest derived bio-based plastics). Most plastics that are currently in development that label themselves as "carbon-negative" are made from carbon dioxide sourced from the waste stream of fossil-fuel combustion which makes production of these so-called "carbon-negative" bioplastics effectively a co-product of fossil fuels.

Accordingly, there is a need for methods and systems for producing true carbon-negative bioplastic.

SUMMARY

Bio-based alternatives to plastic exist, but they are generally developed to prioritize the biodegradability of the final material and with, at best, post-hoc accounting of the greenhouse-gas emissions of their production. Existing algae-based bioplastics still rely on fossil-fuel inputs in the cultivation and harvesting of the algae and in the processing of the algae into useful polymers.

In one aspect, the present disclosure provides for a zero-input aquaculture. In some embodiments, the methods of disclosure employ renewable energy-sources. In some embodiments, the disclosure provides for the production of algae-based plastic that is carbon-negative in the broadest scope. In certain aspects, the disclosure provides for the production of a bioplastic wherein there is less carbon dioxide in the atmosphere because the bioplastic was produced and the carbon dioxide remains removed for timescales meaningful to combatting the worst effects of climate change. In some embodiments, the disclosure provides for carbon dioxide to be sequestered in one or more reservoirs. Examples of such reservoirs of the present disclosure include: in the biomass of the algae in cultivation in saline waters where there would not be photosynthetic activity otherwise, in the silt around the macroalgae cultivation site, in the plastic itself so long as it remains in use, and/or in the soil the algae plastic composts into at its end of life.

In an embodiment, a method of producing a carbon-negative bioplastic comprises combining a hydrocolloid with a volume of water, which forms a solution, homogenizing the solution with a rotor stator disperser, resting the solution, heating the solution, transferring a volume of the solution to a mold, cooling the solution, and dehydrating the solution. The hydrocolloid is derived from algae sourced from an aquaculture. The hydrocolloid is combined with a volume of water by depositing the hydrocolloid into a chamber containing the water through an inlet, forming a solution in the chamber. The rotor stator disperser is submerged into the chamber containing the solution. The solution rests for a time sufficient for a component of the solution to saturate and disperse. The solution is heated to a sufficient temperature and held at the temperature for about 1 to 15 minutes. The volume of the solution is transferred from the chamber through an outlet coupled to a sieve and into a mold. The solution is cooled to a temperature sufficient for the solution to solidify, and then the solution is dehydrated.

In an embodiment, a carbon-negative bioplastic comprises a hydrocolloid, an optical transparency, a tensile strength, and a carbon-negative footprint. The hydrocolloid is sourced from an aquaculture mixed with a volume of water, forming a solution. The tensile strength ranges from about 100 KPa to about 300 KPa. All energy inputs used to produce the carbon-negative bioplastic are renewably sourced.

In some embodiments, at least one source of a compressed or an inert gas may be used to maintain the composition of the mixture of gases in the process chamber in which the carbon0negative bioplastic composition is formulated. The system or apparatus may use one or more sensors to monitor the temperature, pressure, and composition of the mixture of gases in the chamber. The system or apparatus may also use one or more controllers to release the solution and compressed gases into the interior of the chamber wherein a variable rate of release is sufficient to ensure consistent concentrations of the mixture of gases within the chamber.

In some embodiments, the process chamber is a controlled atmosphere container.

A bioreactor system may be provided that produces a carbon-negative bioplastic. The bioreactor system may include a process chamber containing a volume of water. The production of the bioplastic in the process chamber may be controlled by an electronic controller. The electronic controller may be controlled by a host system, such a server. The electronic controller may be configured to direct production of the bioplastic in the process chamber by, for example, controlling the release of hydrocolloid, which is derived from algae, to the volume of water in the process chamber through an inlet on a surface of the process chamber to form a solution.

The controller may cause a rotor stator disperser to homogenize the solution in the process chamber, wherein the rotor stator disperser is submerged into the solution via the inlet on the surface of the process chamber. The controller may control temperature in the process chamber via a heating element configured to heat the solution in the process chamber.

The controller may direct a sieve to facilitate transport of the solution in the process chamber to a mold. The controller may be in communication with a compressor bank coupled to a refrigerator that cools the process chamber. In this way, for example, the controller may control cooling the solution to a temperature sufficient for the solution to solidify. The controller may cause the solution to rest for a time sufficient for at least a component of the solution to saturate and disperse. The controller may cause dehydration of the solution to form a bioplastic having substantially optically transparency and durability.

The controller may control directing culturing of the hydrocolloid in a liquid that is not normally configured to harbor photosynthesis in nature, providing, at least in part, for the bioplastic's carbon-negative property. The hydrocolloid may be at least one of: alginate, agar, or carrageenan.

The controller may directs the sieve to facilitate transport of the solution in the process chamber to a mold further includes the controller directing transfer of the volume of the solution into the mold forms a seal at an area within the mold.

The controller may cause the solution to rest by, for example, resting the solution for up to 15 minutes for the component of the solution to saturate and disperse.

The solution preferably has a concentration from about 0.1% to about 10%, wherein the concentration is a measure of dry mass per solution volume.

Preferably, the controller and other energy based components of the system are powered by renewably sourced electricity, providing the bioplastic's high material consistency and preserving zero emissions output from production.

The controller may facilitate adding a second component to the solution at a concentration from about 0.1% to about 5%, wherein the concentration is a measure of the mass per solution volume.

The controller may cause coating the mold with a material, wherein the material has a binding affinity to the component in the solution. The binding affinity to the component in the solution is a preferably property of a material composition of the component or a geometry of the component.

The mold may be a glass and configured to provide a high material reflectivity. The mold may have a smooth surface configured to resist capillary action, thereby reducing shrinkage during the dehydrating of the solution.

The controller may cause hydration of the solution by controlling airflow, temperature, and relative humidity. The controller may cause purge gas to be emitted in the chamber to reduce impurities in the chamber. The controller can be configured to monitor temperature in the process chamber using temperature sensors. The controller may be configured to monitor pressure via pressure sensors, pressure gauges and pressure transducers in communication with the process chamber.

The controller may direct cooling of the solution in communication by controlling the release of refrigerant in a refrigerator coupled to the process chamber. The controller may cause the temperature of the process chamber to be reduced by varying speed of a drive motor of the refrigerator based on pressure and temperature readings from sensors in the process chamber.

Preferably, the resulting bioplastic has an optical transparency, a tensile strength from about 100 KPa to about 300 KPa; and a carbon-negative footprint, wherein all operational energy inputs to produce the carbon-negative bioplastic are renewably sourced.

The controller may be configured to respond to an over pressure condition by decreasing a temperature setpoint of the process chamber. The compressor bank may include at least one compressor configured to supply the refrigerant to the refrigerator, the refrigerator arranged to consume the refrigerant. The controller may be configured to regulate the refrigerant supply to the refrigerator in response to temperature and pressure readings from the process chamber.

The controller may enable the rotor stator disperser to homogenize the solution in the process chamber using one or more air lift pumps configured to create a radially outward flow within the process chamber to mix the solution.

The controller receiving instructions from a report server system that processes predictive algorithms based on the readings from the process chamber. For example, the predictive algorithms may make recommendations to regulate the rate of release of heat, refrigerant, purge gas or oxygen in the process chamber via a variable rate compressor motor.

Preferably, the bioplastic has substantially optically transparency that allows transmission of about 70% of light to about 100% of light.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

DETAILED DESCRIPTION

Figure 1:
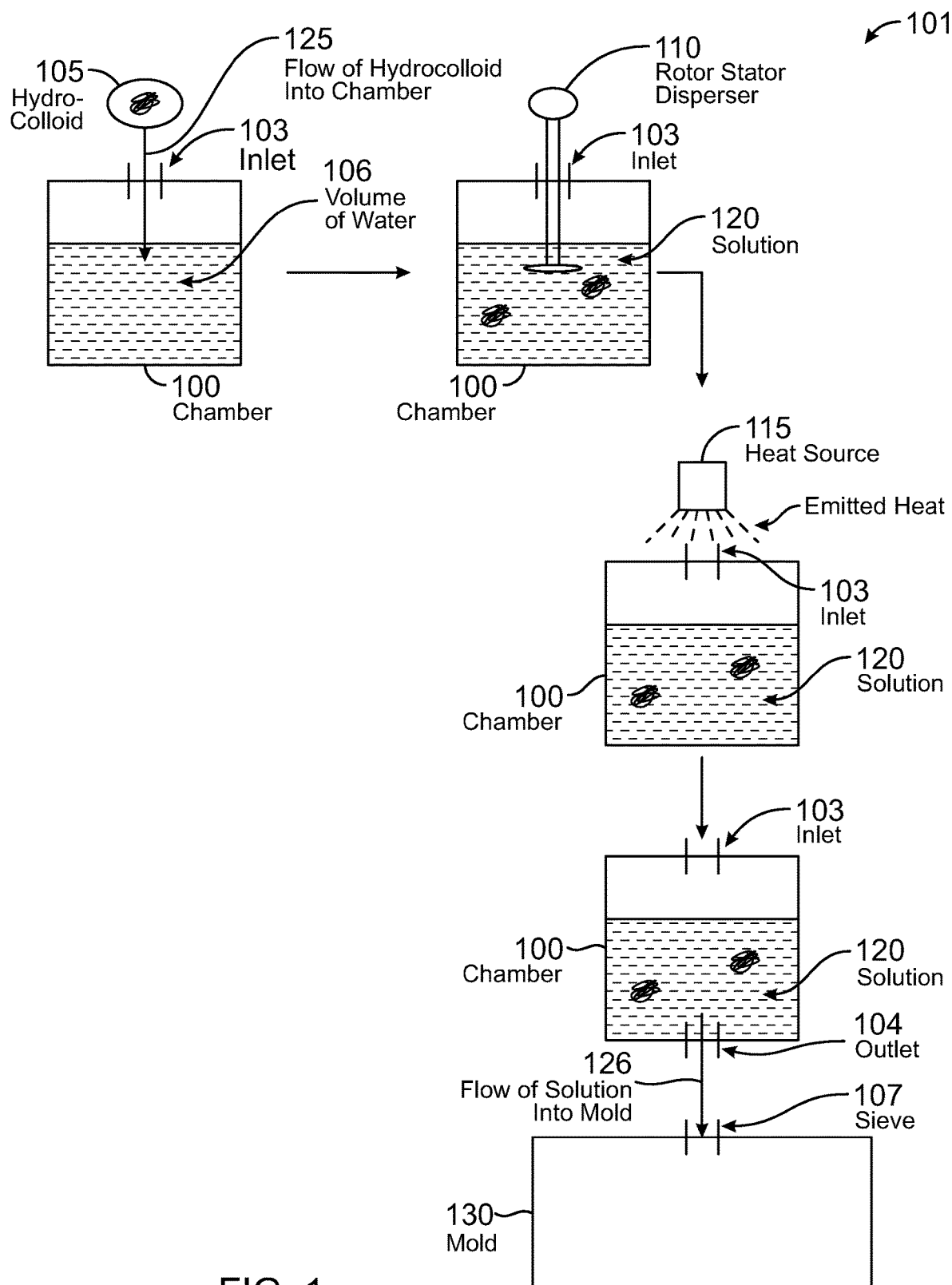
FIG. 1 is a schematic diagram of a carbon-negative bioplastic production process, in accordance with an embodiment of the disclosure.

A description of example embodiments follows.

With overconsumption still on the rise, climate experts predict that by 2050, the fashion industry will be responsible for a considerable percentage of human carbon dioxide emissions. Lab-grown carbon-negative material and methods of producing carbon-negative bioplastics, as disclosed herein, provides for nontoxic materials and positively impacts the material science developments towards advocacy and policy change that protects the environment. Carbon-negative material derived and produced from algae is a material is used in producing materials that do not need to be recycled or cleaned up.

Several aspects of the disclosure are described below, with reference to examples for illustrative purposes only. Specific details, relationships, and methods are set forth to provide a full understanding of the disclosure. One having ordinary skill in the relevant art, however, will readily recognize that the disclosure can be practiced without one or more of the specific details or practiced with other methods, protocols, reagents, aquacultures, or algae. The present disclosure is not limited by the illustrated ordering of acts or events, as some acts may occur in different orders and/or concurrently with other acts or events. Furthermore, not all illustrated acts, steps or events are required to implement a methodology in accordance with the present disclosure. Many of the techniques and procedures described, or referenced herein, are well understood and commonly employed using conventional methodology by those skilled in the art.

Unless otherwise defined, all terms of art, notations and other scientific terms or terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly-used dictionaries, should be interpreted as having a meaning that is consistent with their meaning in the context of the relevant art and/or as otherwise defined herein.

The terminology used herein is for the purpose of describing particular embodiments only and is not intended to be limiting.

As used herein, the indefinite articles "a," "an" and "the" should be understood to include plural reference unless the context clearly indicates otherwise.

Throughout this specification and the claims which follow, unless the context requires otherwise, the word "comprise," and variations such as "comprises" and "comprising", will be understood to imply the inclusion of, e.g., a stated integer or step or group of integers or steps, but not the exclusion of any other integer or step or group of integer or step. When used herein, the term "comprising" can be substituted with the term "containing" or "including."

As used herein, "consisting of" excludes any element, step, or ingredient not specified in the claim element. When used herein, "consisting essentially of" does not exclude materials or steps that do not materially affect the basic and novel characteristics of the claim. Any of the terms "comprising," "containing," "including," and "having," whenever used herein in the context of an aspect or embodiment, can in some embodiments, be replaced with the term "consisting of," or "consisting essentially of" to vary scopes of the disclosure.

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and, therefore, satisfy the requirement of the term "and/or" as used herein. Concurrent applicability of more than one of the options is also understood to fall within the meaning, and, therefore, satisfy the requirement of the term "and/or."

When a list is presented, unless stated otherwise, it is to be understood that each individual element of that list, and every combination of that list, is a separate embodiment.

Methods of Producing Carbon-Negative Bioplastic

FIG. 1 is a schematic diagram of an example carbon-negative bioplastic production process 101, in accordance with an embodiment of the disclosure. The carbon-negative bioplastic production process includes combining a hydrocolloid 105 with a volume of water 106, which forms a solution 120, homogenizing the solution 120 with a rotor stator disperser 110, resting the solution 120, heating the solution 120, transferring a volume of the solution 120 to a mold, cooling the solution 120, and dehydrating the solution 120.

As used herein, the term "carbon-negative" and "carbon-negative" are defined as a process or article of manufacturing, or any activity or byproduct related to originating from the process or article of manufacturing, that emits no carbon and has no measurable carbon footprint. These terms are defined herein to further mean that no carbon is emitted during the method of manufacturing a bioplastic from the start of manufacturing to the disposal of an item made using the manufactured material.

In some embodiments, the hydrocolloid 105 is derived from algae sourced from an aquaculture. In some embodiments the hydrocolloid 105 is alginate, agar, or carrageenan. In some embodiments, the hydrocolloid is derived from an algae, such as *Asparagopsis taxiformis* (*A. taxiformis*), *Asparagopsis armata* (*A. armata*), *Gelidium amansii* (*G. amansii*), *Gelidium pacificum* (*G. pacificum*), *Gelidium sesquipedale* (*G. sesquipedale*), *Ahnpheltia plicata* (*A. plicata*), *Pterocladia capillace* (*P. capillace*), *Pterocladia lucida* (*P. lucida*), *Acanthopheltis japonica* (*A. japonica*), *Ceramiun hypnaeordes* (*C. hypnaeordes*), *Ceranium boydenii* (*C. boydenii*), *Gracilaria gracilis* (*G. gracilis*), *Gracilaria cliftonii* (*G. cliftonii*), *Gracilaria salicornia* (*G. salicornia*), *Gelidiella acerosa* (*G. acerosa*), *Ahnfeltiopsis concinna* (*A. concinna*), *Pterocladiella capillacea* (*P. capillacea*).

In certain embodiments, the algae is sourced from an aquaculture. In some embodiments, algae are cultured in a liquid that is not normally configured to harbor photosynthesis in nature, providing, at least in part, for the bioplastics carbon-negative property.

Suspended offshore aquaculture allows cultivated colonies of algae to increase the net primary productivity of an area of ocean and increases seaweed biomass. Harvesting this biomass allows for continual carbon sequestration in biomass.

In an embodiment, the hydrocolloid 105 is combined with a volume of water 106 by depositing the hydrocolloid 105 into a chamber 100 containing the water through an inlet 103, forming a solution 120 in the chamber 100. The rotor stator disperser 110 is submerged into the chamber 100 containing the solution 120. The solution 120 rests for a time sufficient for a component of the solution 120 to saturate and disperse.

The hydrocolloid is combined with water in a 0.05%-8% concentration (w/v). Rotor/stator emulsion and homogenization at 10,000 to 30,000 rpm for duration between 1 minute and 30 minutes combined with resting between 5 minutes and 8 hours will achieve variable degrees of saturation and dispersion and thereby final material transparency.

In some embodiments, the process chamber may be configured to comprise a pumping or mixing system. One such arrangement is shown in FIG. 6. It should be noted that example implementations of the process 101 of FIG. 1 may be implemented in a mechanical, software, firmware, or hardware environments; FIGS. 1, 3, 5A, 5B, and 6, illustrate such environments.

In certain embodiments, the solution 120 is heated via a heat source 115 to a sufficient temperature. In still further embodiments, the solution 120 is held at the temperature for about 1 to 15 minutes. In some embodiments, the temperature is held for about 1, 2, 3, 4, 5, 6, 7, 8, 9, 10, 11, 12, 13, 14, 15, 16, 17, 18, 19, or 20 minutes. In some embodiments, the temperature is held from about 1 to 5, 1 to 3, 2 to 7, 2 to 10, 4 to 8, 8 to 10, 8 to 12, 8 to 15, 10 to 15, 15 to 20, or 18 to 20 minutes. In some embodiments, the heat source 115 is carbon-neutral. In certain embodiments, the heat source 115 is solar powered, wind powered, water powered, geothermal or a combination thereof.

In some embodiments, the volume of the solution 120 is transferred from the chamber 100 through an outlet 104 coupled to a sieve 107 and into a mold 130. In some embodiments, transferring the volume of the solution 120 into the mold 130 forms a seal at an area within the mold 130. The solution 120 is cooled to a temperature sufficient for the solution 120 to solidify, and then the solution 120 is dehydrated.

In some embodiments resting the solution 120 for up to 15 minutes is sufficient for the component of the solution 120 to saturate and disperse. In some embodiments resting the solution 120 for up to about 8, 9, 10, 11, 12, 13, 14, 15, 16, 17, 18, 19, or 20 minutes.

In some embodiments cooling the solution to below 32-40° C. but not below 0° C. produces solidification. In some embodiments dehydrating the cast, solidified solution is performed at below 40% RH, below 85° C. The dehydration rate is preferably kept slow to improve the final material's ductility.

In some embodiments, the solution 120 has a concentration from about 0.1% to about 10%. In some embodiments, the solution 120 has a concentration of at least about 0.05%, 0.06%, 0.07%, 0.08%, 0.09%, 0.1%, 0.2%, 0.3%, 0.4%, 0.5%, 0.6%, 0.7%, 0.8%, 0.9%, or 10%. In some embodiments, the percentage is measure according to mass per volume. In some embodiments, percentage is measured according to volume per volume. In still other embodiments, percentage is measured according to mass per mass. A person of ordinary skill in the art will readily identify the appropriate method for determining concentration. In some embodiments, the concentration is a measure of dry mass per solution 120 volume.

In some embodiments, as shown in FIGS. 1, 3, 4, 5A, 5B, and 6 the bioplastics production method may be implemented as an algorithmic process in a computer program product 114 stored on a non-transitory computer readable medium configured to facilitate selecting the temperature and/or the timing of the method, the computer program product including computer readable instructions executed by an electronic controller having one or more computer processors, cause the one or more processors to: combine the hydrocolloid with a volume of water; deposit the hydrocolloid into a chamber; form a solution in the chamber; homogenize the solution; rest the solution for a time sufficient for a component of the solution to saturate and disperse; heat the solution to a sufficient temperature; hold the solution at a temperature for a period of time; transfer a volume of the solution in the chamber through an outlet; cool the solution to a temperature sufficient for the solution to solidify; and/or dehydrate the solution.

In certain embodiments, controllers for use in the method may be implemented in a software, firmware, or hardware environment. In some embodiments, the controller may integrate predictive algorithms to combine the hydrocolloid with a volume of water; deposit the hydrocolloid into a chamber; form a solution in the chamber; homogenize the solution; rest the solution for a time sufficient for a component of the solution to saturate and disperse; heat the solution to a sufficient temperature; hold the solution at a temperature for a period of time; transfer a volume of the solution in the chamber through an outlet; cool the solution to a temperature sufficient for the solution to solidify; and/or dehydrate the solution.

In some embodiments, one or more computer processors or the one or more controllers maintain an electronic record, such as a log, of the combination of the hydrocolloid with a volume of water; depositing of the hydrocolloid into a chamber; the formation of a solution in the chamber; the homogenization of the solution; the timing of the rest sufficient for a component of the solution to saturate and disperse; the temperature sufficient to heat the solution; the timing of the holding the solution at a temperature; the volume of transfer of the solution in the chamber through an outlet; the cooling of the solution to a temperature sufficient for the solution to solidify; and/or the dehydrating of the solution.

In some embodiments, homogenizing the solution 120 is powered by renewably sourced electricity, providing the bioplastics high material consistency. High material consistency may be composed of consistent thickness within +/−0.25 mm, total light transmittance of >90% and low surface roughness.

In some embodiments, a second component is added to the solution 120 at a concentration from about 0.1% to about 5%. In some embodiments, second component is added to the solution 120 has a concentration of at least about 0.05%, 0.06%, 0.07%, 0.08%, 0.09%, 0.1%, 0.2%, 0.3%, 0.4%, 0.5%, 0.6%, 0.7%, 0.8%, 0.9%, or 10%. In certain embodiments, the concentration is a measure of the mass per solution 120 volume.

In some embodiments, the mold 130 is coated with a material, wherein the material has a binding affinity to the component in the solution 120. The binding affinity is a property of a material composition of the component or a geometry of the component. In some embodiments, coating the mold with cellulose, rough texture, absorbent material and using angular geometry contribute to low mold fail rates.

In some embodiments, the mold 130 is a glass and is configured to provide high material reflectivity. In some embodiments, the mold 130 has a smooth surface configured to provide resistance to capillary action, thereby reducing shrinkage during dehydrating the solution 120. In some embodiments, dehydrating the solution 120 is performed by controlling airflow, temperature, relative humidity using renewable power, or any combination thereof.

In an embodiment, a carbon-negative bioplastic comprises a hydrocolloid 105, an optical transparency, a tensile strength, and a carbon-negative footprint. The hydrocolloid 105 is sourced from an algae extract mixed with a volume of water 106, forming a solution 120.

In some embodiments, the tensile strength ranges from about 100 KPa to about 300 KPa. In certain embodiments, the tensile strength is about 80, 85, 90, 95, 100, 105, 110, 120, 125, 130, 135, 140, 145, 150, 160, 170, 180, 190, 200, 210, 220, 230, 240, 250, 260, 270, 280, 290, 300, 310, 320, 330, 340, 350, 360, 370, 380, 390, or 400 KPa.

Figure 2:
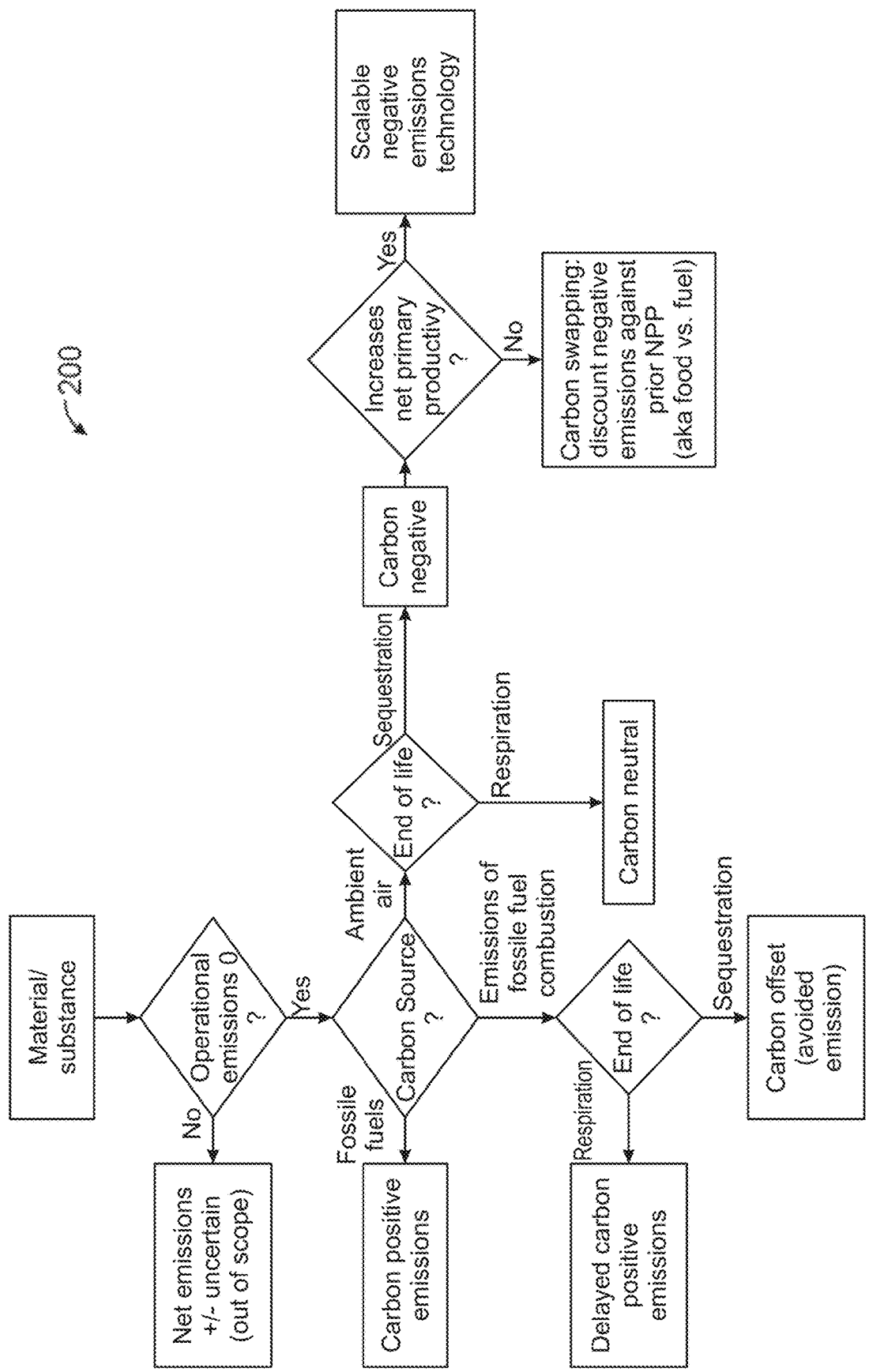
FIG. 2 is a flow diagram detailing a true carbon-negative bioplastic process, in accordance with an embodiment of the disclosure.

In some aspects, the disclosure provides that all energy inputs to produce the carbon-negative bioplastic are renewably sourced from plant materials that do not normally harbor photosynthesis if left in nature. FIG. 2 is a flow diagram detailing a true carbon-negative bioplastic process 200, in accordance with an embodiment of the disclosure.

In some embodiments, the hydrocolloid 105 is alginate, agar, or carrageenan. In some embodiments, the hydrocolloid 105 does not harbor photosynthesis in nature and is derived from an aquaculture. In some embodiments, the optically transparent end-product allows transmission of about 70% of light to about 100% of light. In some embodiments, the optically transparent end-product allows transmission of about 70%, 75%, 80%, 85%, 90%, 95%, 96%, 97%, 98%, 99% or 100% of light.

In an embodiment, a system for producing a carbon-negative bioplastic comprises a chamber containing a volume of water, a rotor stator disperser, a heat source, a sieve, a mold, and an algorithm. A hydrocolloid is added to the volume of water in the chamber through an inlet on a surface of the chamber to form a solution. The rotor stator disperser homogenizes the solution in the chamber. The rotor stator disperser is submerged into the solution via the inlet on the surface of the chamber. The heating element is configured to heat the solution in the chamber. The heating element is renewably sourced. The sieve facilitates transport of the solution in the chamber to a mold. The sieve attaches to the mold, and the solution travels from the chamber through the sieve and into the mold. The algorithm may be configured via an electronic controller to automate the process.

Carbon-Negative Bioplastics

FIG. 2 is an example flow diagram detailing a true carbon-negative bioplastic process 200, in accordance with an embodiment of the disclosure. In some embodiments, the present disclosure provides, inter alia, a carbon-negative bioplastic including a hydrocolloid. In some embodiments, the material comprises a bioplastic material that is fully transparent. In other embodiments, the material comprises a bioplastic material coated with a second material. In some embodiments, the second material is hydrophobic.

In still other embodiments, the bioplastic may optionally comprise other material that is either a naturally occurring additive or a naturally derived additive. In certain embodiments, the carbon-negative bioplastic is optically transparent. In still further embodiments, the bioplastic has zero carbon footprint.

In some embodiments, a carbon-negative bioplastic is prepared by combining predetermined amounts of an algae-derived gelling hydrocolloid, such as alginate, agar, or carrageenan, obtained from a zero-input or renewably powered aquaculture, and processed and shipped using renewable power. The combined components, such as the gelling hydrocolloid and water at a predetermined concentration, are then sheered together with a rotor stator disperser for a predetermined amount of time, the rotor stator disperser being powered by renewably sourced electricity. Algae-derived plasticizers, also referred to herein as a component, are then added to the gelling hydrocolloid and water mixture at a predetermined concentration and allowed to saturate and disperse for a predetermined amount of time.

After the solution saturates and disperses, the solution is heated through either direct heat or a double boiler powered by a renewable energy source. The solution is held at a predetermined temperature for a predetermined time, and then the solution is poured through a sieve into a prepared, leveled glass mold that is either room temperature or pre-heated to above a predetermined temperature using renewable power, if needed. The volume of the solution must be sufficient to fill the mold to its edges and form a seal with the edges of the mold. The mold must be clean of any grease, dust, or lubricant and edged with a material that will bond tightly with the forming gel either through material composition or geometry. The solution must then be allowed to drop below a predetermined temperature to allow a component in the solution to solidify, forming a gel. The gel is then dehydrated over the course of 4-36 hours through the control of airflow, temperature, and relative humidity using renewable power, if needed.

The bioplastic disclosed in some embodiments herein differs from those in the prior art due to its true carbon-negative characteristic. Some manufacturers of bioplastics pull carbon from waste streams of conventional emitters to produce PHA plastics, which leaves a carbon footprint, and vodka, through which its planned use re-emits the carbon, for example. Some manufacturers pull carbon from ambient air and sell the carbon to bottling or greenhouse markets, which causes carbon re-emission, for example. Other manufacturers also pull carbon from ambient air sequester carbon in the final product or material of manufacture, for example but have not done so to produce useful plastic.

The material, method of manufacture, and system disclosed in some embodiments herein are carbon-negative in that carbon is sequestered in the final product or material, carbon is not re-emitted, carbon is not re-emitted through planned use, and no measurable carbon footprint is left behind.

The advantages of producing a bioplastic from a macroalgae include zero carbon emissions, sequestering of carbon, culturing the macroalgae is performed in a dead zone of the ocean, no carbon footprint with respect to the process nor with respect to the end product. The process for culturing and manufacturing a bioplastic, as disclosed herein, is streamlined by way of an algorithm that automates the process carried out by a series of carbon-neutral mechanical components.

In example embodiments, algae-derived sequins are a fragment of a system that allows nature-based carbon capture from the open air to produce a material of value. The biggest missed opportunity in the fashion industry is true decarbonization. A concept of circularity that overemphasizes waste gives one permission to make a new petroleum-derived polymer in parts of the market. There is an urgent need for carbon-negative bioplastics, particularly in the fashion industry.

Figure 7:
FIG. 7 is an example of algae derived plastics in a sequins textile implementation according to an embodiment.

In addition to its advantage as a carbon-sequestration technology, the described novel algae-based plastic has several technical advantages within its material properties when compared to existing examples of algae-based plastic including but not limited to: the clarity of the material, its consistency, its high reflectivity, its dimensional stability from molding through curing, and its neutral scent. In one example, FIG. 7 shows algae derived plastics in a sequins textile implementation according to an embodiment. The algae derived plastics shown in FIG. 7 is developed using the process/algorithm of FIG. 1, evidencing its improved clarity of the material, its improved consistency, its high reflectivity, and improved durability in a sequin representation.

Figure 3:
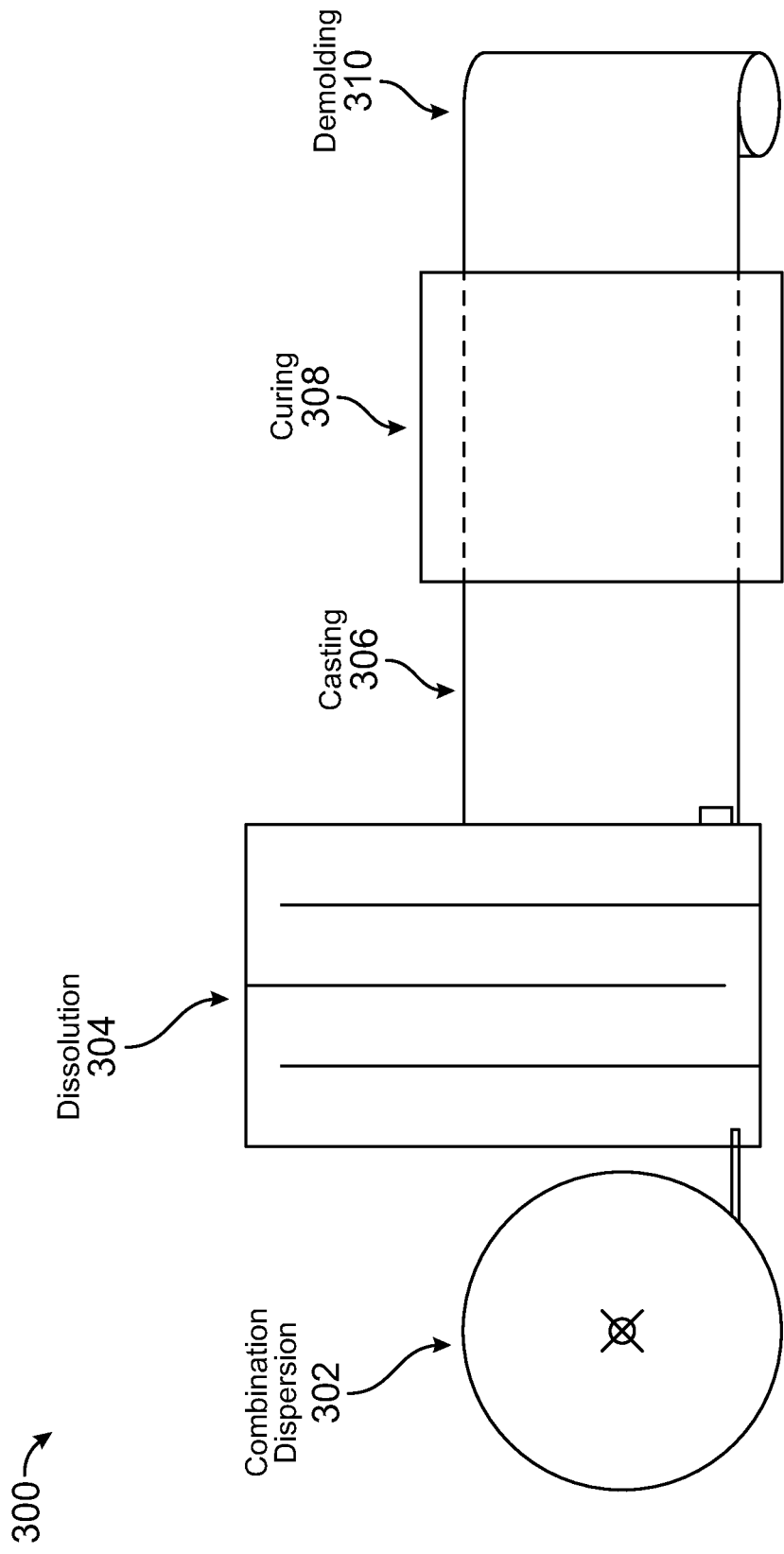
FIG. 3 is a schematic showing an example algorithm defining a process of manufacturing a carbon-negative bioplastic, in accordance with an embodiment of the disclosure.

FIG. 3 is a schematic showing an example algorithm 300 defining a process of manufacturing a carbon-negative bioplastic, in accordance with an embodiment of the disclosure. The manufacturing process may interface with the digital process environments and computing environments shown in FIGS. 5A and 5B. Electronic controller(s) 550, 560 may be used to control the manufacturing process. At 302-310, the formulation of solution combination undergoes dispersion where the process combines the hydrocolloid with a volume of water; deposits the hydrocolloid into a process chamber; forms a solution in the chamber; homogenize and casts the solution at 306 where its rests the solution for a time sufficient for a component of the solution to saturate and disperse, heats the solution to a sufficient temperature and holds the solution at a temperature for a period of time; transfer a volume of the solution in the chamber through an outlet; cool the solution to a temperature sufficient for the solution to solidify; and/or dehydrate the solution.

Figure 4:
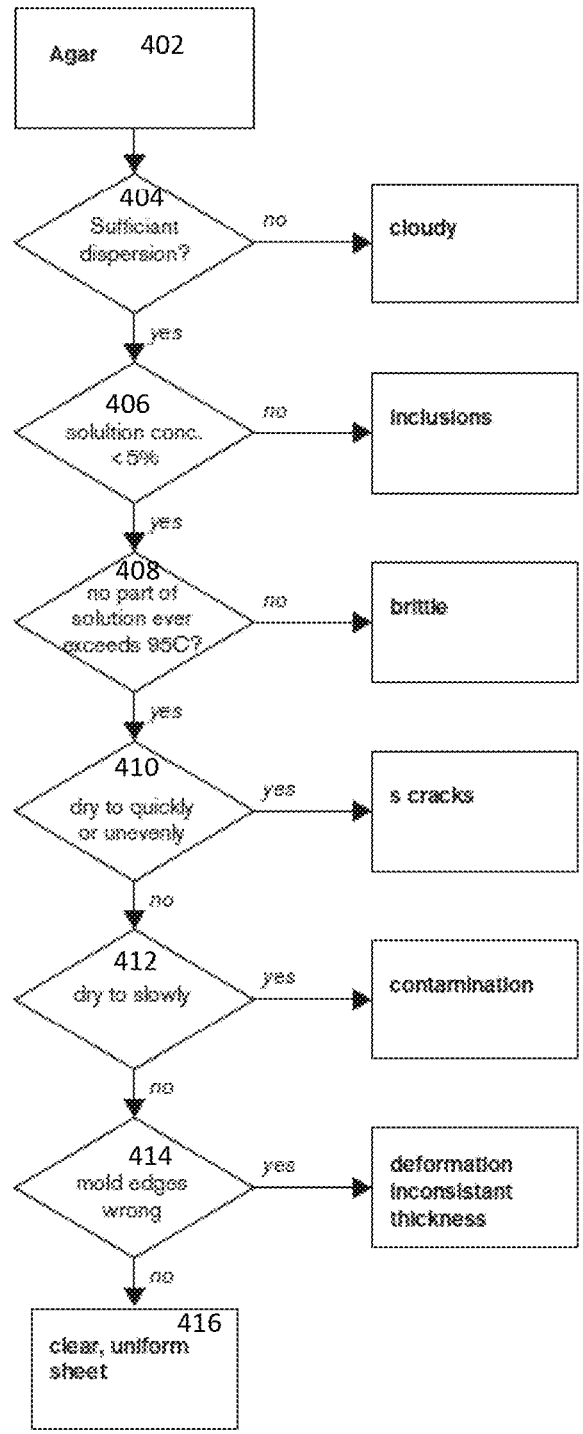
FIG. 4 is a schematic showing an example algorithm defining a process of producing an optically transparent carbon-negative bioplastic, in accordance with an embodiment of the disclosure.

FIG. 4 is a schematic showing an example algorithm defining a process 400 of producing an optically transparent carbon-negative bioplastic, in accordance with an embodiment of the disclosure. This process may be implemented by an electronic controller 550 of FIG. 5A. As shown at 404, the image quality of agar 402 solution is assessed in the process chamber 100 to determine if there is sufficient dispersion. In this way, the process ensures that the solution is without any cloudy characteristics. Computer based image processing techniques 515 and 92, for example, can be used and processed by the controller to assess the transparency or translucence quality of the solution and ensure that it is without trace elements that may obscure the clarity.

At 406, the controller sends instructions to cause the solution to be measured and tested to ensure that it has a concentration of at least about 0.05% of, for example, gelling hydrocolloid and water at a predetermined concentration. A tool in communication with the process chamber can be used to measure the concentration.

At 408, the controller sends instructions to measure temperature via temperature sensors. In this way, the temperature of the solution is measured to ensure that no portion of the solution exceeds 95 C. The preferred temperature is held at predetermined amount of time. The controller ensures that the temperature of the solution does not exceed this threshold. If it exceeds this threshold, the resulting bioplastic is undesirable as it is likely to be brittle and no longer a durable textile.

At 410, the process 200 ensures that the solution does not dry too quickly and unevenly. Pumping systems, such as those in FIG. 6, may be activated by the controller to facilitate this process. Exhaust and ventilation systems may also be utilized by the controller. Variable rate pumping, purging, and ventilation may be utilized to ensure that the solution does not dry to quickly or unevenly. In this way, the electronic controller 550 of FIG. 5A may be used to control variable rate pumping, purging, and ventilation processes. If the solution dries too quickly or unevenly, then it is likely to be susceptible to cracking.

The controller may execute predictive algorithms to ensure that the solution does not dry to quickly or unevenly. The controller may causes the chamber to maintain the ultra low oxygen concentration in the event of a sudden leak or influx of atmospheric gas from the exterior or interior of the container. Oxygen levels may be monitored to ensure that they are a desirable level. For example, in some circumstances, it may be desirable to maintain an ultra low oxygen concentration in the chamber, e.g. less than 4,000 ppm or less than 2,000 ppm to ensure that the solution does not dry to quickly or unevenly or spoil.

In some embodiments, the controller may integrate predictive algorithms to regulate the rate of release of heat, refrigerant, purge gas or oxygen. In embodiments, the controller may regulate release of heat, refrigerant and gas via a variable rate compressor motor. The regulation of release of the variable rate motor may be operated at a rate which anticipates leakage of heat or cold air, or other sources of contribution of oxygen. In other embodiments, the controller may be coupled to an oxygen sensor to minimize or shut off stored compressed gas release when the oxygen level is at or below a minimum set point.

At 412, the controller ensures that the solution does not dry too slowly. If it dries too slowly, it is susceptible to contamination. As in 410, the controller may integrate predictive algorithms to regulate the rate of release of heat, coolant, purge gas or oxygen. In embodiments, the controller may regulate release of the gas at a rate which anticipates leakage or other sources of contribution of oxygen. In other embodiments, the controller may be coupled to an oxygen sensor to minimize or shut off stored compressed gas release when the oxygen level is at or below a minimum set point.

At 414, the volume of the solution is assessed via the controller to ensure that it is at capacity to fill the mold to its edges and form a seal with the edges of the mold. The controller uses image processing algorithms and scans to determine that the mold is any grease, dust, or lubricant and edged with a material that will bond tightly with the forming gel either through material composition or geometry. If the mold is correctly filled to its edges, then a clear uniform sheet 416 is provided. Embodiments to perform the image processing algorithms may include means for encoding, tracking, modeling, filtering, tuning, decoding, or displaying video or data signal information.

Algae Bioplastics Algorithms Digital Processing Environments

Figure 5A:
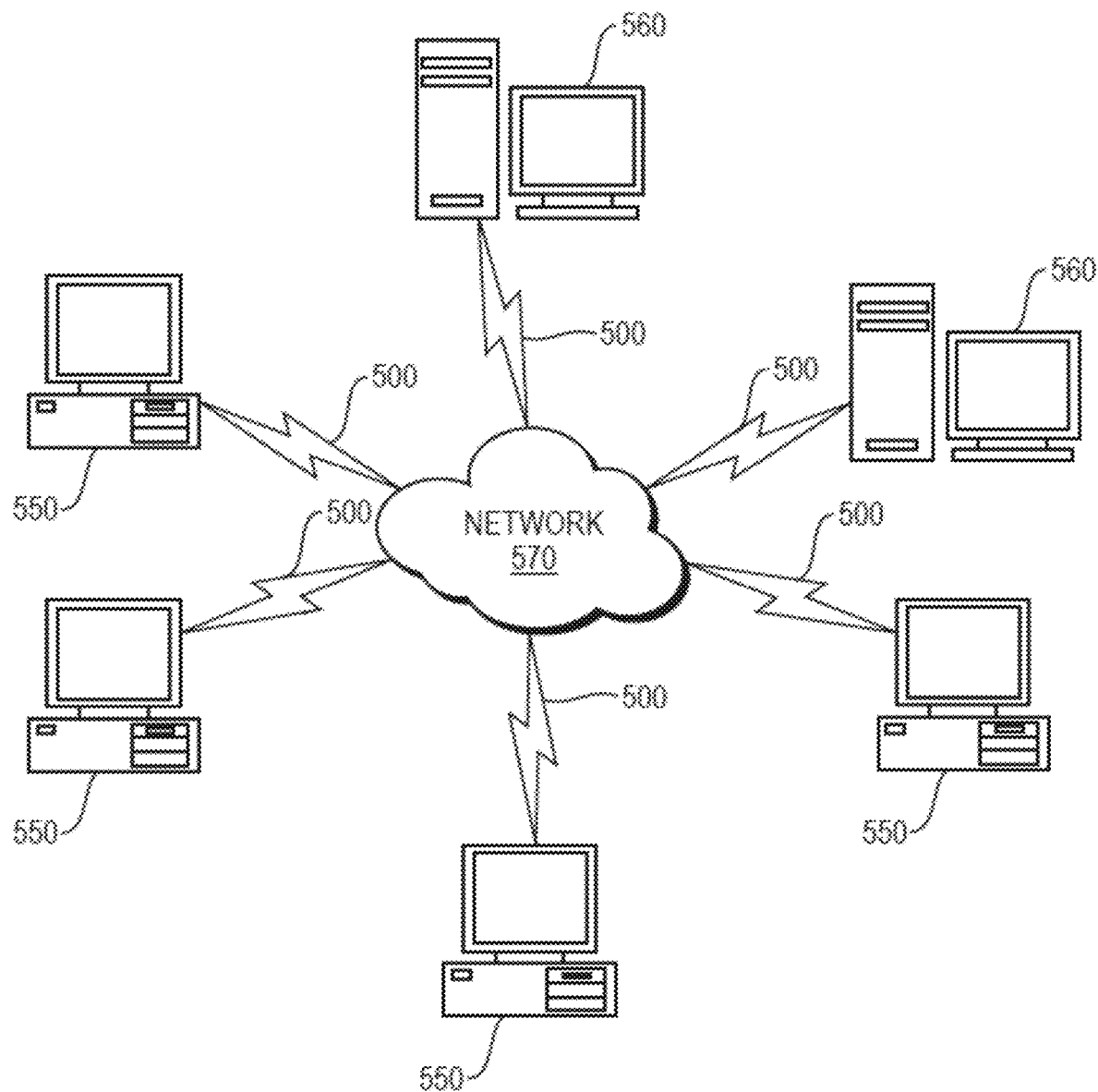
FIG. 5A is a block diagram of any internal structure of an electronic controller/computing node according to an embodiment.
Figure 5B:
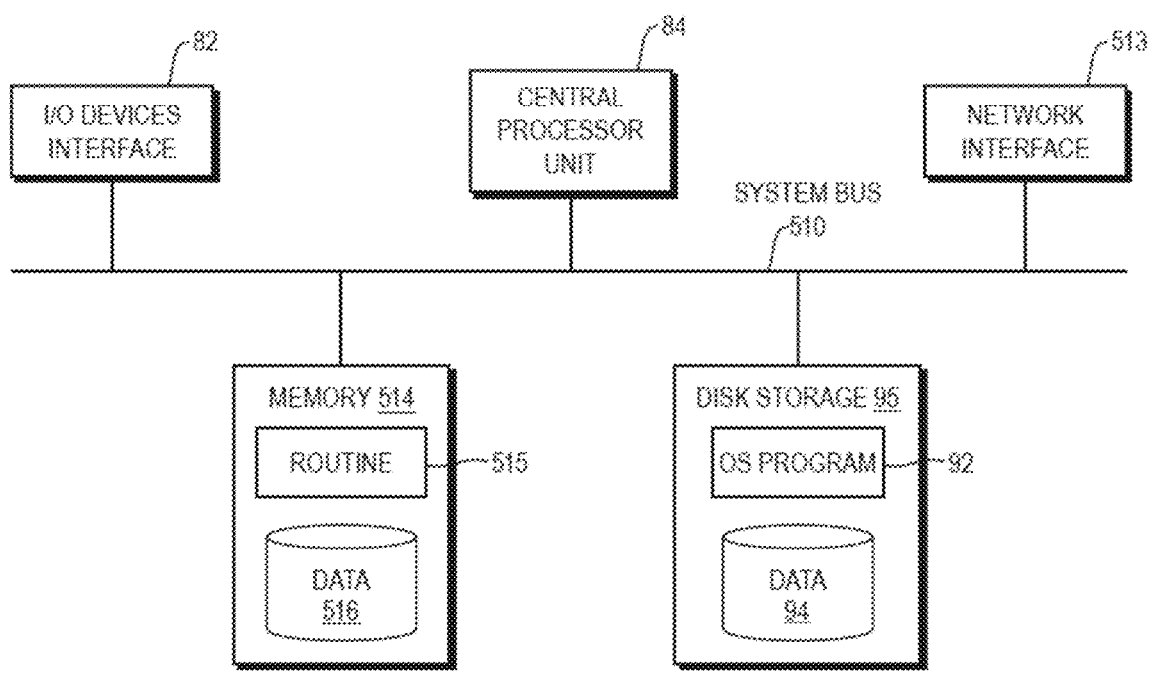
FIG. 5B is a block diagram showing an example according to an embodiment.
Figure 6:
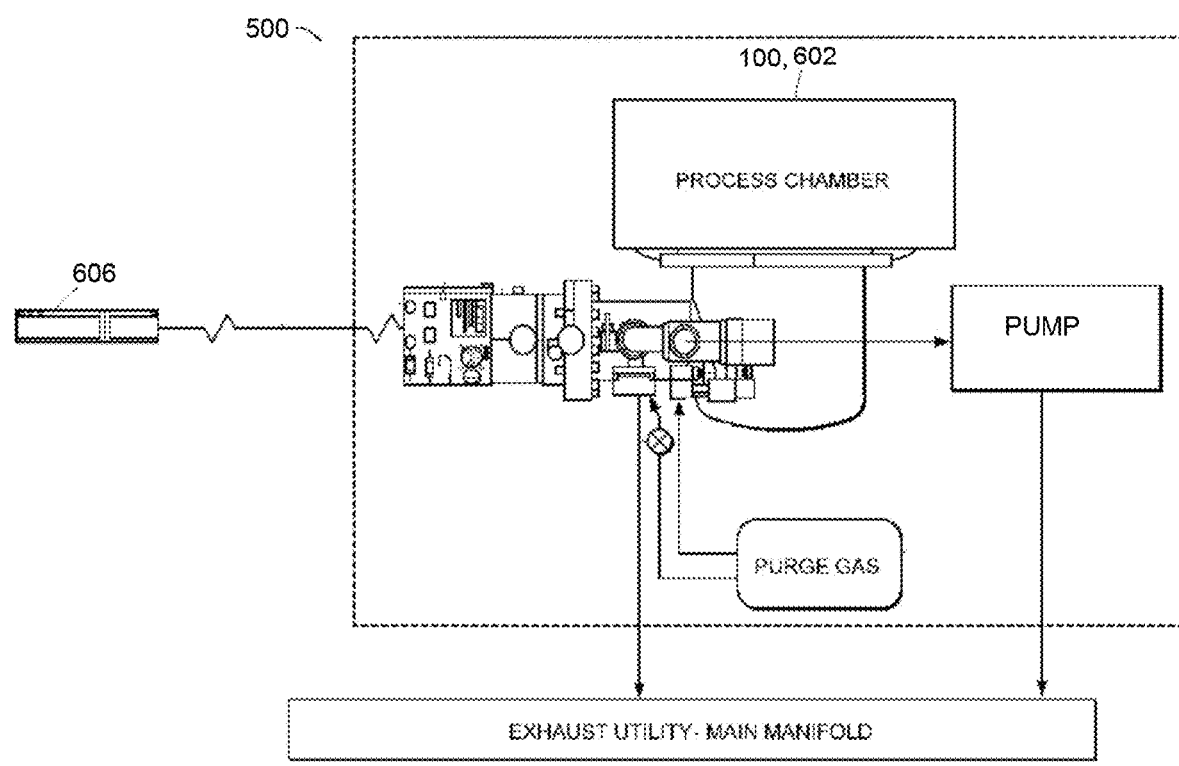
FIG. 6 is a computer implemented example algae bioplastics processing system according to an embodiment.

FIG. 5B is a block diagram of any internal structure of a computer/computing node (e.g., client processor/device 550 or server computers 560) in the processing environment of FIG. 5A, which may be used to implement software algorithms that produce bioplastics according to an embodiment. It should be noted that the processing environment of FIGS. 5A, 5B and 6 should be utilizing data centers entirely on locally-sourced carbon-free energy. The bioplastics may be produced in a cleanroom environment, such as the process chamber 100, 602 shown in FIG. 6. The process chamber 100, 602 may be interconnected with a vacuum, such as a roughing pump, waterpump, or cryopump to remove substances and particulars from the chamber. Inert gas, such as purge gas may be used to dilute and purge particles and gases from the chamber and facilitate the removal of the gases and undesirable particulars including dust during the pumping process. This can enable the bioplastic to be free of foreign particles and be substantially composed of algae without foreign bodies. The chamber may be implemented with temperature sensors to enable the controllers 550, 560 to monitor temperature and implement the processes/algorithms embodied in FIG. 1.

Each computer 550, 560 in FIG. 5B contains a system bus 510, where a bus is a set of actual or virtual hardware lines used for data transfer among the components of a computer or processing system. The system bus 510 is essentially a shared conduit that connects different elements of a computer system (e.g., processor, disk storage, memory, input/output ports, etc.) that enables the transfer of data between elements.

Attached to the system bus 510 is an I/O device interface 82511 for connecting various input and output devices (e.g., keyboard, mouse, touch screen interface, displays, printers, speakers, audio inputs and outputs, video inputs and outputs, microphone jacks, etc.), such as input devices 82 to the computer or electronic controller 550, 560. A network interface 513 allows the electronic controller to connect to various other devices, such as pumping systems, attached to a network (for example the network illustrated at 570 of FIG. 5A and 606 of FIG. 6). Memory 514 provides volatile storage for computer software instructions 515 and data 516 used to implement some embodiments of the invention.

In an example mobile implementation, a mobile agent implementation of the invention may be provided to interface with input devices 82. A client server environment can be used to enable mobile security services using the server 560. It can use, for example, the XMPP protocol to tether software enabling an electronic controller 550 that interfaces 500 with a server system 560 that provides instructions to an electronic controller 550 enabling production of a bioplastic 515 in a bioplastic processing system 500. The server 560 can then issue commands to the controller on request. A mobile user interface framework may be used to access certain components of the system, and may implemented in XHP, Javelin and WURFL. In another example mobile implementation for OS X and iOS operating systems and their respective APIs, Cocoa and Cocoa Touch may be used to implement the client-side components 515 using Objective-C or any other high-level programming language that adds Smalltalk-style messaging to the C programming language.

The system may also include instances of server processes on the server computers 560 that may comprise cloud system, which allow registering a user, selecting switches and input devices 82 for configuring.

Disk storage 95 provides non-volatile storage for computer software instructions 515 (equivalently "OS program") and data 516 and 94 used to implement embodiments of a system to facilitate producing algae based bioplastic according to an embodiment of the present disclosure. The system may include disk storage 95 accessible to the server computer 560. The server computer can maintain secure access to records related to the authentication of users registered to control the input devices 82. Central processor unit 84 is also attached to the system bus 510 and provides for the execution of computer instructions.

In an example embodiment, the processor routines 515 and data 92 are computer program products. Aspects of the system for producing algae based bioplastic 500 according to an embodiment may include both server-side and client-side components.

Software implementations 515, 92 may be implemented as a computer readable medium capable of being stored on a storage device 95, which provides at least a portion of the software instructions for electronic controller 550 and input devices 82. Executing instances of respective software components to configure the input devices 82, such as instances of configuration engine, may be implemented as computer program products 515, and can be installed by any suitable software installation procedure, as is well known in the art. In another embodiment, at least a portion of the system software instructions 515 may be downloaded over a cable, communication and/or wireless connection via, for example, a browser SSL session or through an app (whether executed from a mobile or other computing device). In other embodiments, software components 515, may be implemented as a computer program propagated signal product embodied on a propagated signal on a propagation medium (e.g. a radio wave, an infrared wave, a laser wave, a sound wave, or an electrical wave propagated over a global network 570, 606 such as the Internet, or other networks. Such carrier medium or signal provides at least a portion of the software instructions.

It should be noted that while technologies exist that claim to be "carbon-negative", it appears that most of such technologies are misusing the phrase and are not truly carbon-negative.

Figure 8:
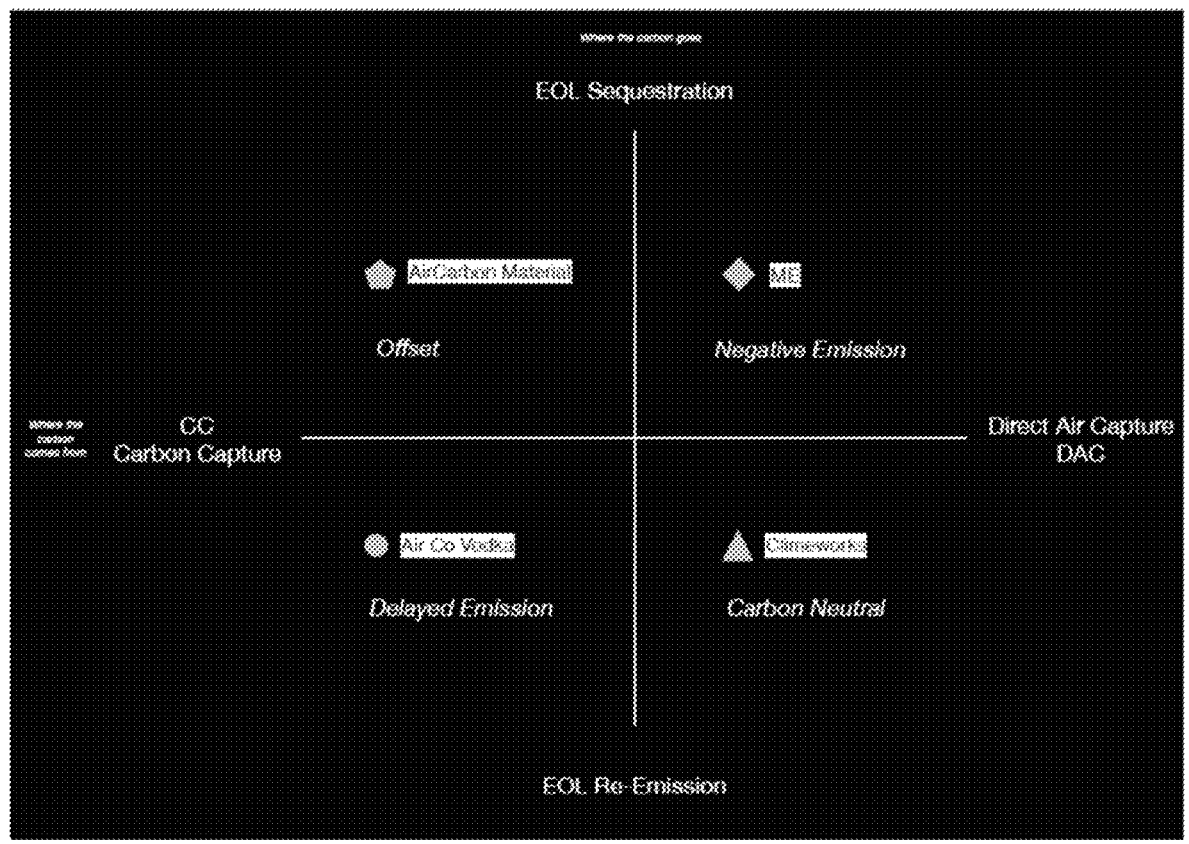
FIG. 8 shows example instances of categories of Direct Air Capture Utilization and Storage (DACUS) uses of the term carbon-negative.

FIG. 8, for example, shows instances of categories of Direct Air Capture Utilization and Storage (DACUS) uses of the term "carbon-negative". AirCarbon techniques exist that from PHB and PHB that pulls carbon from waste streams to make PHA plastic. AirCo techniques exists that pull carbon from waste streams of conventional emitters; vodka is made which through its planned use re-emits carbon. Climeworks pulls carbon from ambient air, and sells carbon into b the bottling greenhouse market, which causes re-emission. CX Algae Plastic pulls carbon from ambient air, and carbon is sequestered in the final material. None of these conventional approaches relate to textiles or algae. While such techniques shown in FIG. 8 claim to be "carbon-negative", they are not truly carbon-negative in the context of some embodiments of the present disclosure.

For example, there are some textile based approaches that claim to be carbon-negative, but they typically do not account for the emissions that result from the base textile. For those that use algae in the textile, when the algae dies, its carbon will respire back into the air and, therefore, the use of the algae is not carbon-negative as suggested. Moreover, the textiles that use algae lack the clarity of the carbon-negative bioplastic derived using the innovations set forth in the present disclosure.

Biogarmetry fabric exists, for example, that that sequesters CO2, via conventional silk or rayon with micro algae growing on its surface. This implementation does not, for instance, account for the emissions of the base textile. Further, the fabric lacks optical clarity and it is not truly "algae-based". It should be noted that typical technologies that claim to be "algae-based" often contain nominal content, such as 5% algae content. US20130186303A1 appears typical with long lists of biopolymers that are presented as interchangeable (including agar) with no evidence that agar was successfully used in this way or used in a meaningful concentration. If agar is used in the same way as starches or gelatins in such formulations, the material tears itself apart as it dries and, and as such, durability is comprised.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A bioreactor system to produce a bioplastic from macroalgae, the bioreactor system comprising:
   a process chamber with a surface having an inlet, the process chamber including a temperature sensor and a pressure sensor;
   a rotor stator disperser;
   a variable rate compressor motor;
   a refrigerator including a drive motor;
   a heating element;
   a sieve;
   a mold; and
   an electronic controller configured to:
   control release of hydrocolloid, which is derived from the macroalgae, to a volume of water in the process chamber through the inlet on the surface of the process chamber to form an agar solution;
   cause the rotor stator disperser to homogenize the agar solution in the process chamber, wherein the rotor stator disperser is submerged into the agar solution via the inlet on the surface of the process chamber;
   request a temperature reading from the temperature sensor in the process chamber to measure the temperature of the homogenized agar solution;
   execute predictive algorithms to control the variable rate compressor motor based on temperature, pressure, and air quality readings in the process chamber to regulate a rate of release of heat, refrigerant, purge gas or oxygen in the process chamber via the variable rate compressor motor;

respond to a measured temperature that exceeds a threshold temperature by causing the temperature of the process chamber to be reduced by varying speed of the drive motor of the refrigerator based on pressure readings from the pressure sensor and temperature readings from the temperature sensor in the process chamber;

request instructions from the predictive algorithms for an assessment of image quality of the agar solution for cloudy characteristics to identify impurities of low optical transparency;

respond to the measured temperature and the assessment from the predictive algorithms, by controlling temperature in the process chamber via the heating element, the heating element configured to heat the homogenized agar solution in the process chamber;

direct the sieve to facilitate transport of the homogenized, heated agar solution in the process chamber to the mold;

control cooling the homogenized, heated, molded agar solution to a temperature sufficient for the homogenized, heated, molded agar solution to solidify;

cause the homogenized, heated, molded, solidified agar solution to rest for a time sufficient for at least a component of the homogenized, heated, molded, solidified agar solution to saturate and disperse; and cause dehydration of the homogenized, heated, molded, solidified agar solution to form a bioplastic having substantial optical transparency and durability.

2. The bioreactor system of claim 1, wherein the electronic controller is further configured to:
direct culturing of the hydrocolloid in a liquid that is not normally configured to harbor photosynthesis in nature, providing, at least in part, for a carbon-negative property of the bioplastic.

3. The bioreactor system of claim 1, wherein the hydrocolloid is at least one of alginate, agar, or carrageenan.

4. The bioreactor system of claim 1, wherein the electronic controller is further configured to:
direct transfer of a volume of the homogenized, heated agar solution into the mold forming a seal at an area within the mold.

5. The bioreactor system of claim 1, wherein the electronic controller is further configured to:
cause the homogenized, heated, molded, solidified agar solution to rest for up to 15 minutes.

6. The bioreactor system of claim 1, wherein the agar solution has a concentration from about 0.1% to about 10% of agar, and wherein the concentration is a measure of dry mass per solution volume.

7. The bioreactor system of claim 1, wherein the electronic controller is powered by renewably sourced electricity, providing high material consistency for the bioplastic and preserving zero emissions output from production.

8. The bioreactor system of claim 1, wherein the electronic controller is further configured to:
direct adding of a second component to the agar solution at a concentration from about 0.1% to about 5%, wherein the concentration is a measure of mass per volume of the agar solution.

9. The bioreactor system of claim 1, wherein the electronic controller is further configured to:
direct coating of the mold with a material, wherein the material has a binding affinity to a component in the homogenized, heated agar solution.

10. The bioreactor system of claim 9, wherein the binding affinity to the component in the homogenized, heated agar solution is a property of a material composition of the component or a geometry of the component.

11. The bioreactor system of claim 1, wherein the mold is a-glass and is configured to provide a high material reflectivity, and wherein the mold has a smooth surface configured to resist capillary action, thereby reducing shrinkage during the dehydration of the homogenized, heated, molded, solidified agar solution.

12. The bioreactor system of claim 1, where, in causing dehydration of the homogenized, heated, molded, solidified agar solution, the electronic controller is configured to:
control airflow, temperature, and relative humidity.

13. The bioreactor system of claim 1, wherein the electronic controller is further configured to, during a cooling operation:
direct cooling of the homogenized, heated, molded agar solution by controlling a release of a refrigerant in the refrigerator, the refrigerator coupled to the process chamber.

14. The bioreactor system of claim 1, wherein:
the bioplastic has a tensile strength from about 100 KPa to about 300 KPa, and a carbon-negative footprint; and
all operational energy inputs to produce the bioplastic are renewably sourced.

15. The bioreactor system of claim 1, wherein the electronic controller is further configured to:
respond to an over pressure condition by decreasing a temperature setpoint of the process chamber.

16. The bioreactor system of claim 1, further comprising:
a compressor bank having at least one compressor configured to supply a refrigerant to the refrigerator, the refrigerator arranged to consume the refrigerant; and
wherein the electronic controller is further configured to:
regulate refrigerant supply to the refrigerator in response to temperature and pressure readings from the process chamber; and
cause the rotor stator disperser to homogenize the agar solution in the process chamber using one or more air lift pumps configured to create a radially outward flow within the process chamber to mix the agar solution.

17. The bioreactor system of claim 1, wherein the electronic controller is further configured to:
receive instructions from a remote server system that processes the predictive algorithms to control the variable rate compressor motor based on temperature, pressure, and air quality readings in the process chamber to regulate a rate of release of heat, refrigerant, purge gas or oxygen in the process chamber via the variable rate compressor motor.

18. The bioreactor system of claim 1, wherein the bioplastic having substantial optical transparency allows transmission of about 70% of light to about 100% of light.

19. The bioreactor system of claim 1, wherein the macroalgae is cultured in a dead zone of an ocean.

* * * * *

UNITED STATES PATENT AND TRADEMARK OFFICE
CERTIFICATE OF CORRECTION

Page 1 of 1

PATENT NO. : 12,391,773 B2
APPLICATION NO. : 17/646601
DATED : August 19, 2025
INVENTOR(S) : Charlotte Trumbull McCurdy It is certified that error appears in the above-identified patent and that said Letters Patent is hereby corrected as shown below:

In the Claims

In Column 16, Claim 11, Line 11, please delete "a-" before "glass".

Signed and Sealed this
Thirtieth Day of September, 2025

John A. Squires
*Director of the United States Patent and Trademark Office*